(12) United States Patent  (10) Patent No.: US 7,455,640 B2
Suzuki et al.  (45) Date of Patent: Nov. 25, 2008

(54) ULTRASONIC DIAGNOSTIC APPARATUS

(75) Inventors: Takao Suzuki, Yokohama (JP); Hisashi Hagiwara, Yokohama (JP); Yoshinao Tannaka, Aiko-gun (JP); Yoshinobu Watanabe, Yokohama (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 10/560,375

(22) PCT Filed: Jun. 10, 2004

(86) PCT No.: PCT/JP2004/008468

§ 371 (c)(1),
(2), (4) Date: Dec. 12, 2005

(87) PCT Pub. No.: WO2004/110280

PCT Pub. Date: Dec. 23, 2004

(65) Prior Publication Data

US 2006/0173309 A1 Aug. 3, 2006

(30) Foreign Application Priority Data

Jun. 13, 2003 (JP) .............................. 2003-169909

(51) Int. Cl.
*A61B 8/00* (2006.01)

(52) U.S. Cl. ................ 600/437; 600/440; 600/443; 600/453; 600/450

(58) Field of Classification Search .............. 600/437, 600/440, 443, 453, 450
See application file for complete search history.

(56) References Cited

U.S. PATENT DOCUMENTS 5,619,995 A 4/1997 Lobodzinski
(Continued)

FOREIGN PATENT DOCUMENTS

EP 1 557 125 7/2005
(Continued)

*Primary Examiner*—Eric F Winakur
*Assistant Examiner*—Katherine L Fernandez
(74) *Attorney, Agent, or Firm*—Hamre, Schumann, Mueller & Larson, P.C.

(57) ABSTRACT

A tomographic image and a tissue characteristic image that are in conformity with each other in terms of time-phase and positional relationships can be displayed superimposedly, thereby providing an excellent ultrasonic diagnostic apparatus that enables an easy and detailed observation of a relationship between a structure and a characteristic of a subject tissue. During an operation of ultrasonic wave transmission/reception (in a live mode), a control part (100) allows a tomographic image to be renewed continuously, displayed on a monitor (107), and stored in a tomographic image memory (110), while allowing an elastic modulus image as a tissue characteristic image to be renewed per heartbeat, displayed on the monitor, and stored in an elastic-modulus-image memory (111) as a tissue characteristic image memory. During a suspension of ultrasonic wave transmission/reception (in a cine mode), the control part (100) allows the elastic modulus image to be read out from the elastic-modulus-image memory and the tomographic image that is in synchronization with the elastic modulus image to be read out from the tomographic image memory, and allows these images to be displayed on the monitor.

9 Claims, 10 Drawing Sheets

U.S. PATENT DOCUMENTS

| | | |
|---|---|---|
| 5,840,028 A | 11/1998 | Chubachi et al. |
| 6,159,151 A | 12/2000 | Bonnefous |
| 6,371,912 B1 * | 4/2002 | Nightingale et al. ........ 600/437 |
| 6,398,736 B1 * | 6/2002 | Seward ....................... 600/466 |
| 6,558,324 B1 * | 5/2003 | Von Behren et al. ........ 600/440 |
| 6,749,571 B2 * | 6/2004 | Varghese et al. ............ 600/450 |
| 6,979,294 B1 * | 12/2005 | Selzer et al. ................ 600/450 |

FOREIGN PATENT DOCUMENTS

| | | |
|---|---|---|
| JP | 5-317313 A | 12/1993 |
| JP | 7-075636 | 3/1995 |
| JP | 10-5226 | 1/1998 |
| JP | 2000-60853 | 2/2000 |
| JP | 2000-229078 | 8/2000 |
| JP | 2004-215968 | 8/2004 |

\* cited by examiner

ULTRASONIC DIAGNOSTIC APPARATUS

TECHNICAL FIELD

The present invention relates to an ultrasonic diagnostic apparatus that displays a superimposed tomographic image and tissue characteristic image.

BACKGROUND ART

Conventional ultrasonic diagnostic apparatuses have a configuration in which the intensity of a reflection echo signal obtained as a result of ultrasonic wave irradiation onto a subject is converted into a luminance of a corresponding pixel so that the structure of the subject is displayed in the form of a tomographic image. Further, in recent years, there has been an attempt to measure a movement of a subject precisely by analyzing a phase of a reflection echo signal so as to determine an elastic modulus of the subject based on a result of the measurement.

As Conventional Example 1, a method has been proposed in which high-precision tracking is performed by determining an instantaneous position of a subject using both an amplitude and a phase of an output signal obtained as a result of detection of a reflection echo signal so that minute vibrations in a large amplitude displacement motion caused due to pulsations are captured (see, for example, JP10(1998)-005226 A).

Furthermore, as Conventional Example 2, a method and an apparatus that are based on a development of the method according to Conventional Example 1 have been proposed. The method is such that, with respect to a large amplitude displacement motion of each of inner and outer surfaces of a blood vessel wall caused due to heartbeats, precise tracking for determining a motion speed of minute vibrations superimposed on the large amplitude displacement motion is performed so that a local elastic modulus of the blood vessel wall is determined based on a difference in the motion speed. The apparatus performs a display in such a manner that a spatial distribution of an elastic modulus is superimposed on a tomographic image (see, for example, JP2000-229078 A).

However, Conventional Example 2 described above makes no mention of a method for displaying an elastic modulus image and a tomographic image and an operation of the apparatus. According to Conventional Example 2 described above, in order to measure an elastic modulus, it is necessary to determine an amplitude of minute vibrations by performing tracking of a movement of a blood vessel wall caused in one heartbeat interval. That is, an elastic modulus image is changed only once per heartbeat. It follows, therefore, that since one heartbeat takes about one second, an elastic modulus image has a frame rate of about one frame per second. Meanwhile, generally, a tomographic image is displayed at 15 to 30 frames per second. Thus, when a display is performed in such a manner that an elastic modulus image is superimposed simply on a tomographic image, due to a large difference in frame rate, it is unclear to which portion an elastic modulus corresponds, which has been problematic.

DISCLOSURE OF INVENTION

In view of the above-described conventional problem, it is an object of the present invention to provide an excellent ultrasonic diagnostic apparatus that can display a superimposed tomographic image and tissue characteristic image such as an elastic modulus image that are in conformity with each other in terms of time-phase and positional relationships during a suspension of ultrasonic wave transmission/reception, namely, in a cine mode, thereby enabling an easy and detailed observation of a relationship between a structure and a characteristic of a subject tissue.

In order to achieve the above-mentioned object, an ultrasonic diagnostic apparatus according to the present invention includes: ultrasonic wave transmission/reception means that transmits/receives an ultrasonic wave with respect to a subject; a tomographic image processing part that forms a tomographic image representing a structure of the subject based on a reception signal; a tissue characteristic processing part that forms a tissue characteristic image representing a physical characteristic of a tissue of the subject through analysis of the reception signal; memory means (tomographic image memory, tissue characteristic image memory) that stores the tomographic image and the tissue characteristic image, respectively; an image composing part that combines at least the tomographic image and the tissue characteristic image; display means that displays at least the tomographic image and the tissue characteristic image; and control means that, during an operation of ultrasonic wave transmission/reception (in a live mode), allows the tomographic image to be renewed in an arbitrary cycle, displayed by the display means, and stored in the memory means, while allowing the tissue characteristic image to be renewed in a cycle different from the cycle for the tomographic image, displayed by the display means, and stored in the memory means, and during a suspension of ultrasonic wave transmission/reception (in a cine mode), allows arbitrary one of the tissue characteristic images that have been acquired previously and one of the tomographic images that is in synchronization with the tissue characteristic image to be read out from the memory means, respectively and displayed by the display means.

According to this configuration, in a live mode, a tomographic image can be obtained in real time, and thus a probe operation such as for positioning and operations of setting various values such as a gain can be performed easily, and in a cine mode, a tomographic image and a tissue characteristic image can be obtained that are in conformity with each other in terms of time-phase and positional relationships between a structure and a characteristic of a subject tissue.

In the ultrasonic diagnostic apparatus configured as above, preferably, the display means is divided into a first display region and a second display region, and displays at least the tomographic image in the first display region and at least the tomographic image on which the tissue characteristic image is superimposed in the second display region. During the operation of ultrasonic wave transmission/reception, the control means allows the tomographic image to be displayed at least in the first display region of the display means, while allowing the tissue characteristic image to be displayed in the second display region of the display means, and during the suspension of ultrasonic wave transmission/reception, the control means allows the tissue characteristic image and one of the tomographic images that is in synchronization with the tissue characteristic image to be read out from the memory means, respectively and displayed at least in the second display region of the display means.

According to this configuration, a display screen is divided into two, and thus a portion hidden by a tissue characteristic image also can be viewed at the same time. Therefore, in a live mode, a probe operation such as for positioning and operations of setting various values such as a gain can be performed more easily. Further, in a cine mode, a tomographic image and a tissue characteristic image that coincide with each other in time phase can be obtained at the same time, and thus by comparing the tomographic image with the tissue characteristic image, a relationship between a structure and a characteristic of a subject tissue can be grasped easily.

Furthermore, preferably, during the operation of ultrasonic wave transmission/reception, one of the tomographic images that is in synchronization with the tissue characteristic image is displayed in the second display region. According to this configuration, even in a live mode, a tomographic image and a tissue characteristic image that are in conformity with each other in terms of a positional relationship between a structure and a characteristic of a subject tissue are displayed in a second display region, thereby allowing a diagnosis result to be obtained immediately.

Furthermore, preferably, during the suspension of ultrasonic wave transmission/reception, one of the tomographic images that is in synchronization with the tissue characteristic image is displayed in the first display region. According to this configuration, in a cine mode, a tomographic image and a tissue characteristic image that coincide with each other in time phase can be obtained at the same time, and thus by comparing the tomographic image with the tissue characteristic image, a relationship between a structure and a characteristic of a subject tissue can be grasped easily.

Furthermore, preferably, during the suspension of ultrasonic wave transmission/reception, the tissue characteristic image that is obtained based on a time period in which the tomographic image displayed in the first display region is included and the tomographic image that is in synchronization with the tissue characteristic image are displayed superimposedly in the second display region. According to this configuration, a tomographic image can be displayed frame by frame in a first display region, thereby allowing a detailed examination of a dynamic structural change of a subject tissue in a time period used for calculation of a characteristic of the tissue.

Furthermore, preferably, the image composing part allows a related waveform that contains information corresponding to at least one of the tomographic image and the tissue characteristic image to be displayed on a display screen of the display means in such a manner as to be combined with the tomographic image and the tissue characteristic image, and during the suspension of ultrasonic wave transmission/reception, the control means allows a portion of the related waveform to be displayed in a highlighted manner, which corresponds to a time period in which the tissue characteristic image being displayed is formed. According to this configuration, it is possible to establish a visual correspondence between a tissue characteristic image and a portion of an electrocardiographic waveform or a phonocardiographic waveform that corresponds to a time period in which the tissue characteristic image is formed.

Furthermore, preferably, a tissue characteristic is an elastic modulus. According to this configuration, an elastic modulus image can be obtained that represents hardness/softness of a subject tissue and is in conformity in terms of a positional relationship with a tomographic image representing a structure of the tissue.

As an alternative, preferably, a tissue characteristic is a strain or a strain rate. According to this configuration, a characteristic of a subject tissue can be shown excellently that represents deformability of the tissue and is in conformity in terms of a positional relationship with a tomographic image representing a structure of the tissue.

As an alternative, preferably, a tissue characteristic is a viscosity. According to this configuration, a characteristic of a subject tissue can be shown excellently that represents a viscosity of the tissue and is in conformity in terms of a positional relationship with a tomographic image representing a structure of the tissue.

DESCRIPTION OF THE INVENTION

Hereinafter, the present invention will be described by way of preferred embodiments with reference to the appended drawings.

In each of the embodiments of the present invention, the description is directed to the case in which a tissue characteristic image is an elastic modulus image. However, the present invention is not limited thereto and is applicable to any tissue characteristic image of a subject tissue that is acquired in a cycle different from a cycle for a tomographic image such as an image representing a strain, a strain rate, a viscosity or the like of a tissue.

Embodiment 1

Figure 1:
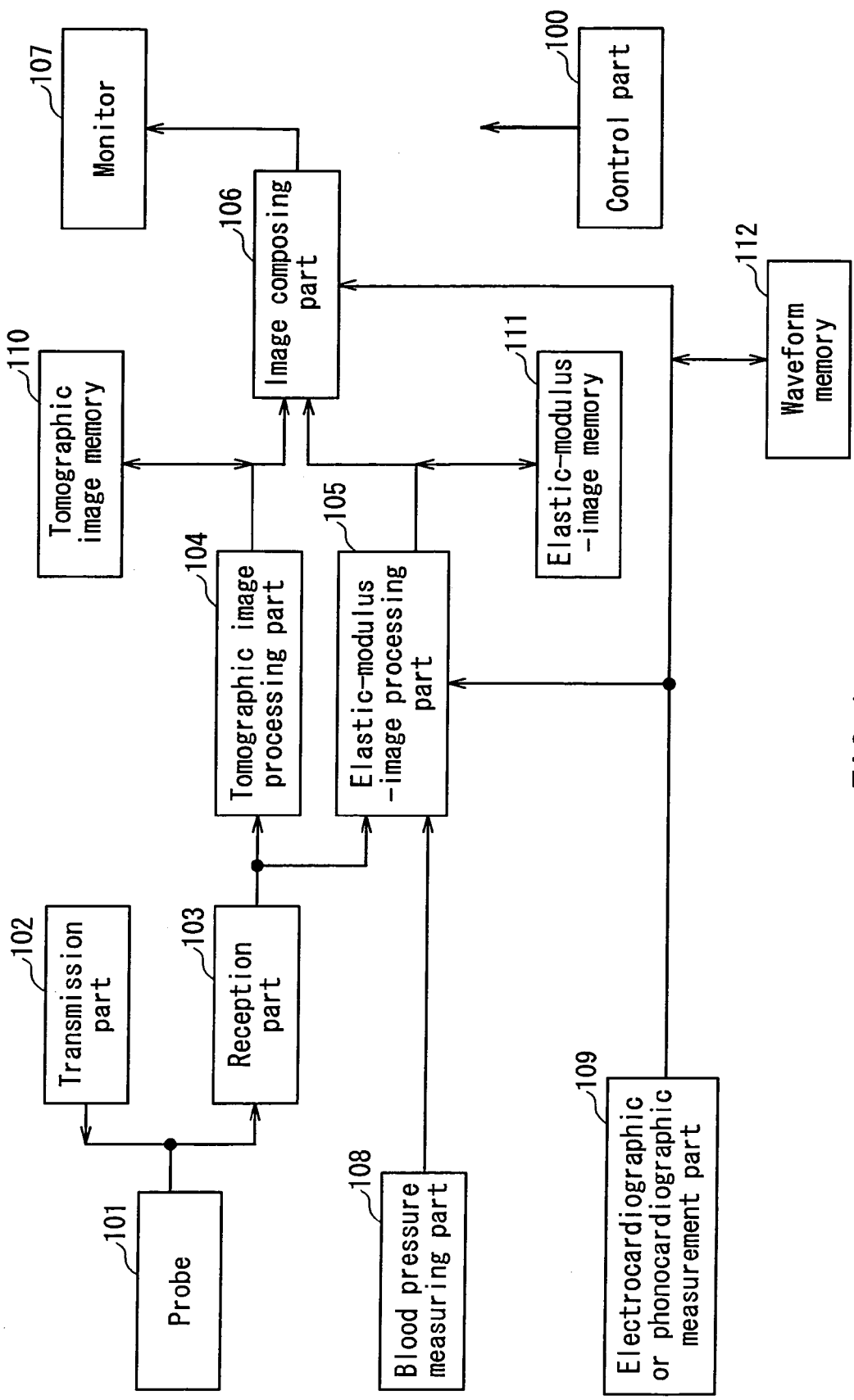
FIG. 1 is a block diagram showing an example of a configuration of an ultrasonic diagnostic apparatus according to each of embodiments of the present invention.

FIG. 1 is a block diagram showing an example of a configuration of an ultrasonic diagnostic apparatus according to Embodiment 1 of the present invention. In FIG. 1, a control part 100 as control means controls operations of the entire ultrasonic diagnostic apparatus. This control relates to all operations such as setting of various parameters for signal processing, control of transmission/reception timing, live/cine mode switching by pressing of a freeze key, mode control, and control of a screen display.

Upon reception of an instruction from the control part 100, a transmission part 102 drives a probe 101. The probe 101 converts a transmission drive signal from the transmission part 102 into an ultrasonic wave and irradiates the ultrasonic wave to a subject, while converting an ultrasonic echo reflected from inside the subject into an electric signal. A reception part 103 amplifies a reception signal, while detecting only an ultrasonic wave from a predetermined position/direction.

A tomographic image processing part 104 is composed of a bandpass filter, a logarithmic amplifier, a wave detector and the like and forms an image representing an internal structure of the subject. Generally, a tomographic image is formed at 15 to 30 frames per second. In this embodiment, an elastic modulus is used as a tissue characteristic representing a physical characteristic of a tissue. Accordingly, an elastic-modulus-image processing part 105 that is a tissue characteristic image processing part measures, based on a reception signal, a strain of a subject tissue caused due to a change in blood pressure, calculates a local elastic modulus of the tissue based on a difference in blood pressure measured in a blood pressure measuring part 108 and the strain, and forms an image representing a result of the calculation. In this embodiment, an elastic modulus is calculated by using, for example, the algorithm disclosed in Conventional Example 2. That is, a movement of the tissue caused in one heartbeat interval is tracked so that a strain of the tissue is determined, and an elastic modulus is calculated based on a maximum blood pressure and a minimum blood pressure that occur in one heartbeat interval. That is, an elastic modulus image is formed once per heartbeat.

An image composing part 106 combines a tomographic image formed in the tomographic image processing part 104, an elastic modulus image formed in the elastic-modulus-image processing part 105, and an electrocardiographic waveform or a phonocardiographic waveform obtained in an electrocardiographic or phonocardiographic measurement part 109, allowing these combined images to be displayed on a monitor 107 as display means. Further, a tomographic image memory 110 and an elastic-modulus-image memory 111 as memory means store a tomographic image and an elastic modulus image, respectively, and a waveform memory 112 stores a phonocardiographic waveform or an electrocardiographic waveform.

The following describes an operation of the ultrasonic diagnostic apparatus having the above-described configuration in further detail with reference to FIGS. 2 to 5.

Figure 2:
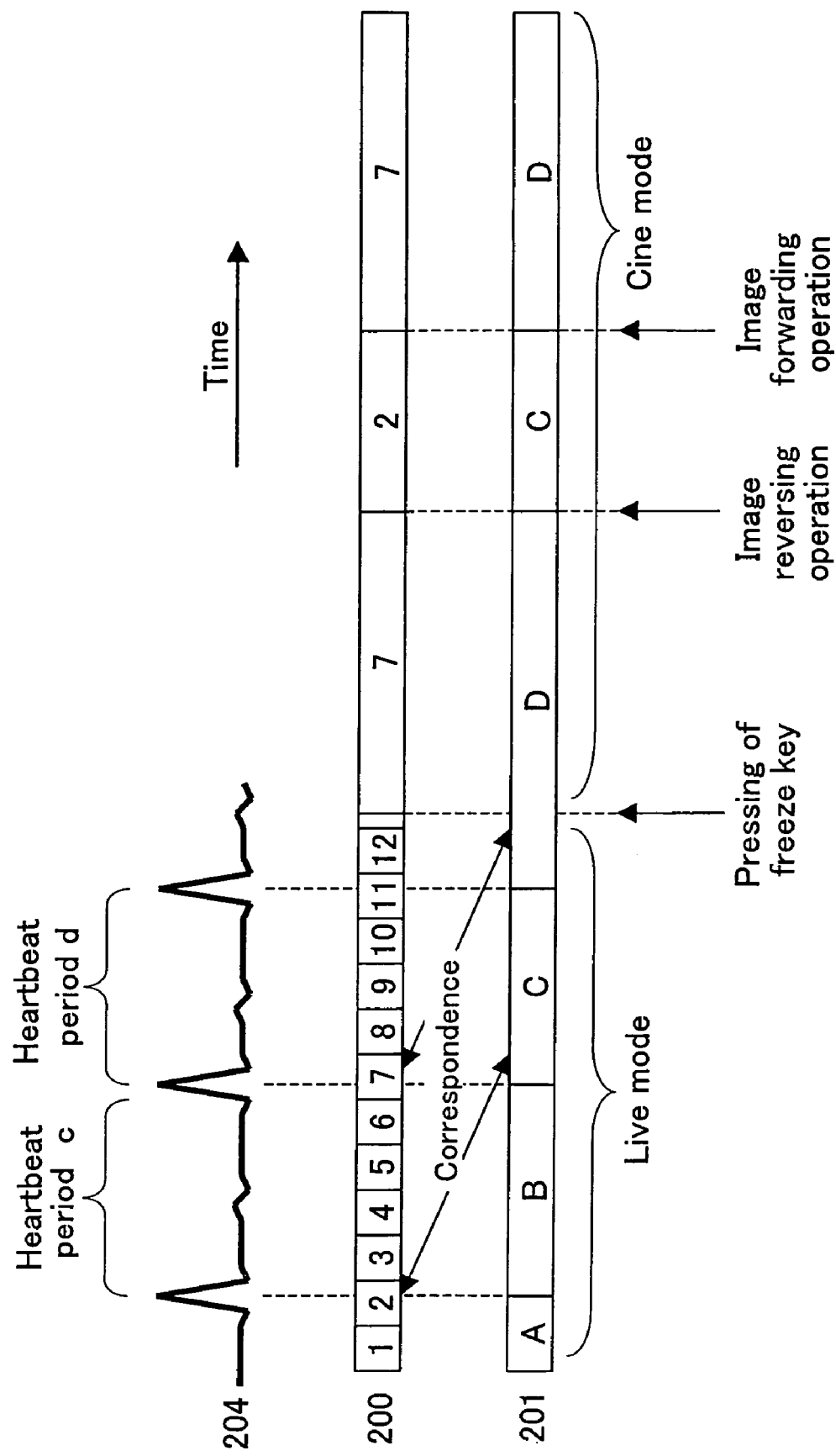
FIG. 2 is a timing chart showing an electrocardiographic or phonocardiographic waveform, tomographic image display frames, elastic-modulus-image display frames according to Embodiment 1 of the present invention.

FIG. 2 is a timing chart showing an electrocardiographic waveform 204, display frames of a tomographic image 200, and display frames of an elastic modulus image 201, which are displayed on the monitor 107 in a state where data is changed during an operation of ultrasonic wave transmission/reception (hereinafter, referred to as a live mode) and a state where previous data is referred to during a suspension of ultrasonic wave transmission/reception (hereinafter, referred to as a cine mode).

Figure 3:
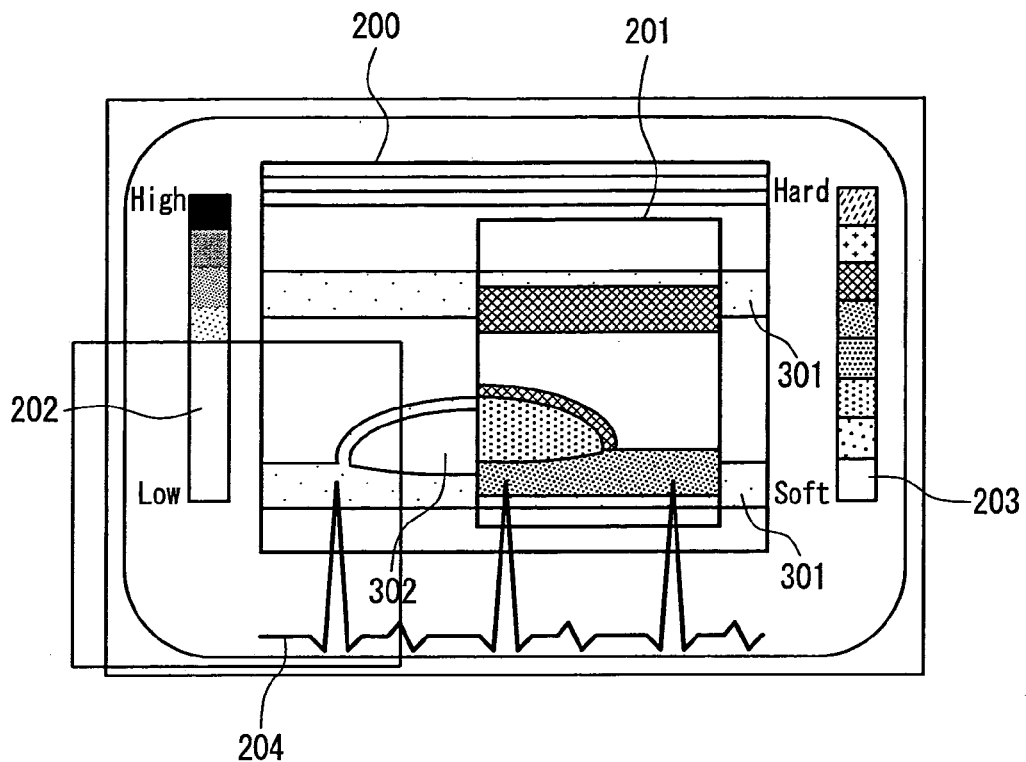
FIG. 3 is a diagram showing an example of a monitor display screen in a live mode illustrated in FIG. 2.
Figure 4:
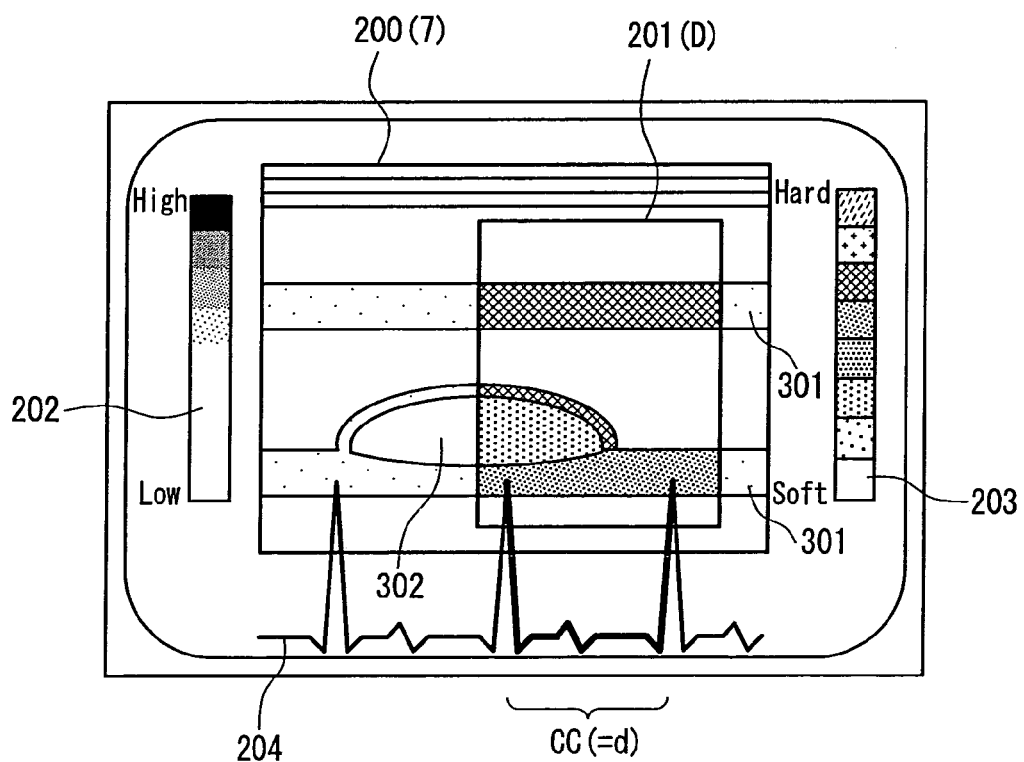
FIG. 4 is a diagram showing an example of a monitor display screen right after being frozen as illustrated in FIG. 2.
Figure 5:
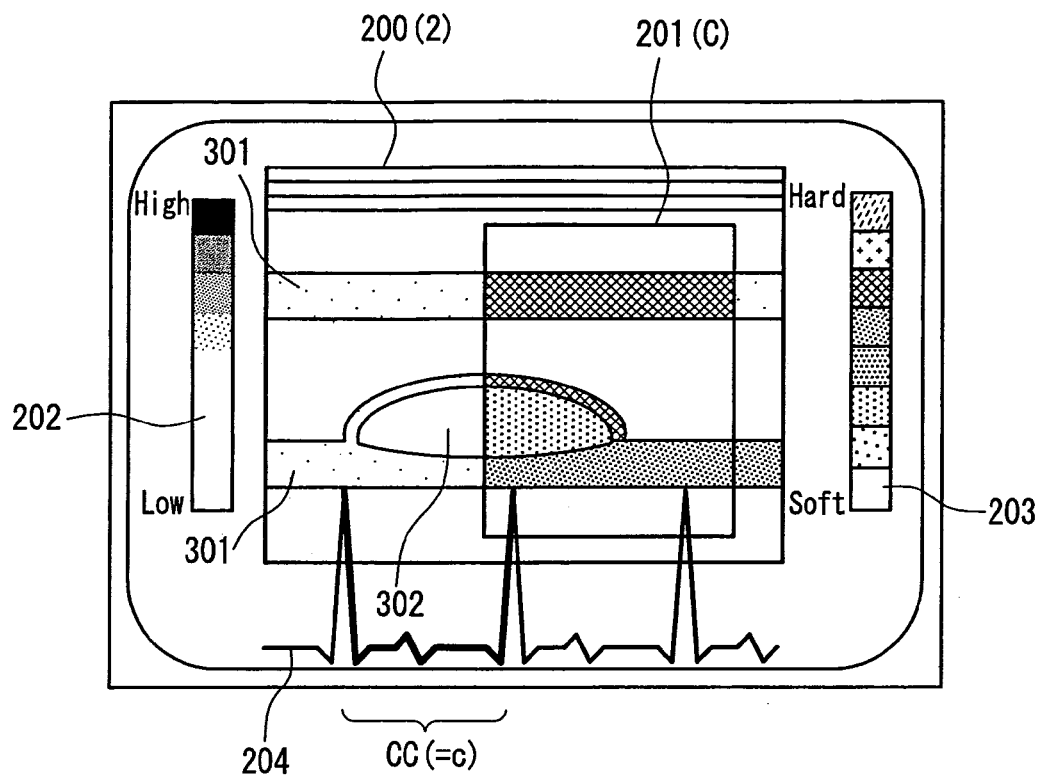
FIG. 5 is a diagram showing an example of a monitor display screen in a cine mode illustrated in FIG. 2.

FIG. 3 shows a display screen of the monitor 107 in the live mode shown in FIG. 2. FIG. 4 shows a display screen of the monitor 107 right after being shifted to the cine mode by pressing of a freeze key. FIG. 5 shows a display screen of the monitor 107 in the case where an image reversing operation is performed in the cine mode shown in FIG. 2.

As shown in each of FIGS. 3 to 5, on a display screen of the monitor 107, the elastic modulus image 201 is displayed in such a manner as to be superimposed on the tomographic image 200. Further, on the display screen, a reflection intensity scale 202 that shows a correspondence between an reflection intensity of the tomographic image 200 and a luminance on the screen, an elastic modulus scale 203 that shows a correspondence between an elastic modulus and a color tone or a luminance on the screen, an electrocardiographic or phonocardiographic image 204, and the like are displayed. As an example, the tomographic image 200 and the elastic modulus image 201 shown in each of FIGS. 3 to 5 show across section along a longitudinal axis of a blood vessel (blood vessel wall 301) having an atheroma 302.

The following description is made in accordance with the timing shown in FIG. 2.

Firstly, in the live mode, the tomographic image 200 is changed continuously at 15 to 30 frames per second so that a newest image is displayed at all times. Meanwhile, the elastic modulus image 201 to be displayed in such a manner as to be superimposed on the tomographic image 200 is formed by calculation of an elastic modulus based on a strain of a tissue and a difference in blood pressure that are caused in one heartbeat interval, and thus is changed in synchronization with a heartbeat, so that the elastic modulus image 201 obtained in a heartbeat period preceding by one heartbeat interval is displayed. Although the tomographic image 200 that is in correspondence with the elastic modulus image 201 in terms of time-phase and positional relationships (hereinafter, expressed as being "in synchronization") is one of images obtained in one heartbeat period, an initial tomographic image is assumed to be used herein.

That is, referring to FIG. 2, a elastic-modulus-image display frame C is formed using an elastic modulus calculated based on a reception signal obtained in a heartbeat period c, and thus only a tomographic image display frame 2 that is obtained initially in the heartbeat period c is in synchronization with the elastic-modulus-image display frame C. Consequently, in the live mode, there is no coincidence between an elastic modulus represented by the elastic modulus image 201 and a tissue structure represented by the tomographic image 200.

In the live mode, the tomographic image 200 and the elastic modulus image 201 are stored in the tomographic image memory 110 and the elastic modulus memory 111, respectively. Further, a phonocardiographic or electrocardiographic waveform obtained in the electrocardiographic or phonocardiographic measurement part 109 is displayed continuously on the screen and stored in the waveform memory 112.

Next, right after a shift to the cine mode is performed in which ultrasonic wave transmission/reception is suspended by pressing of the freeze key, as shown in FIG. 4, a newest image as the elastic modulus image 201 and one of the tomographic images 200 that is in synchronization with the newest image are displayed on the monitor 107. Referring to FIG. 2, a display frame D (denoted by 201(D)) of the newest image as the elastic modulus image 201 at a point of time when the freeze key is pressed, is an elastic modulus image formed based on a strain caused in a heartbeat period d. Therefore, a display frame 7 (200(7)) of a tomographic image as the tomograhic image 200 that is obtained initially in the heartbeat period d and is in synchronization with the frame D is read out from the tomographic image memory 110 and is displayed on the monitor 107. Further, as shown in FIG. 4, a portion of the electrocardiographic or phonocardiographic waveform 204 that corresponds to a heartbeat period CC (=d) in which the elastic-modulus-image display frame 201(D) is formed is displayed in a highlighted manner by means of a change in luminance or color tone (shown by a bold line in the figure).

In the cine mode, it is possible to refer to a previous image by performing an image reversing/forwarding operation. In this embodiment, only an elastic-modulus-image display frame and a tomographic image display frame that is in synchronization therewith are read out from the elastic-modulus-image memory 111 and the tomographic image memory 110, respectively, and are displayed. Referring to FIG. 2, when an image reversing operation is performed, the immediately preceding display frame C (201(C)) of the elastic modulus image 201 is read out from the elastic-modulus-image memory 111, while the display frame 2 (200(2)) of the tomographic image 200 that is in synchronization with the elastic-modulus-image display frame 201(C) is read out from the tomographic image memory 110, and these frames are displayed.

As shown in FIG. 5, the elastic-modulus-image display frame 201(C) and the tomographic image display frame 200 (2) are displayed as superimposed, and a portion of the electrocardiographic or phonocardiographic waveform 204 that corresponds to a heartbeat period CC (=c) in which an elastic modulus image being displayed is formed is displayed in a highlighted manner by means of a change in luminance or color tone (shown by a bold line in the figure).

Referring to FIG. 2, when an image forwarding operation is performed subsequently, the elastic-modulus-image display frame D that immediately follows the elastic-modulus-image display frame C is read out from the elastic-modulus-image memory 111, while the tomographic image display frame 7 that is in synchronization with the elastic-modulus-image display frame D is read out from the tomographic image memory 110, and these frames are displayed on the monitor 107.

As described above, according to this embodiment, in a live mode, a tomographic image can be obtained in real time, and thus a probe operation such as for positioning and operations of setting various values such as a gain can be performed easily, and in a cine mode, a tomographic image and an elastic modulus image can be obtained that are in conformity with each other in terms of time-phase and positional relationships between a structure and an elastic modulus of a subject tissue.

By enabling ON/OFF switching between superimposed and non-superimposed states of the elastic modulus image 201 on the tomographic image 200, the relationship between an elastic modulus and a structure can be grasped more easily.

Figure 6:
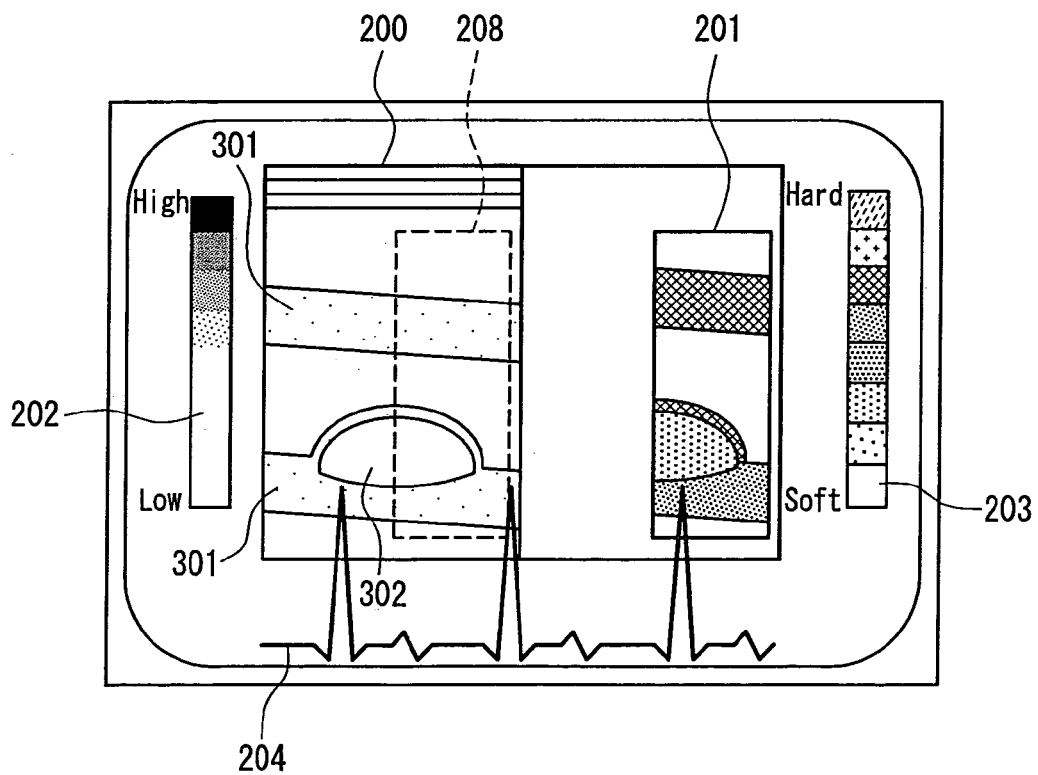
FIG. 6 is a diagram showing an example of a monitor display screen according to a modification of Embodiment 1 of the present invention.

Moreover, the same effect also can be obtained by, as shown in FIG. 6, displaying only a region (ROI: Region of Interest) 208 to be examined on the tomographic image 200 using a broken line, and displaying an image as the elastic modulus image 201 that corresponds to the ROI 208 in a separate region.

Embodiment 2

The following describes an ultrasonic diagnostic apparatus according to Embodiment 2 of the present invention. The ultrasonic diagnostic apparatus according to this embodiment has the same configuration as shown in FIG. 1 referred to in the description of Embodiment 1. A difference from Embodiment 1 is that a display screen of a monitor 107 is divided into two, and only a tomographic image is displayed in one display region (left-side display region), and a tomographic image on which an elastic modulus image 201 is superimposed is displayed in the other display region (right-side display region).

Figure 7:
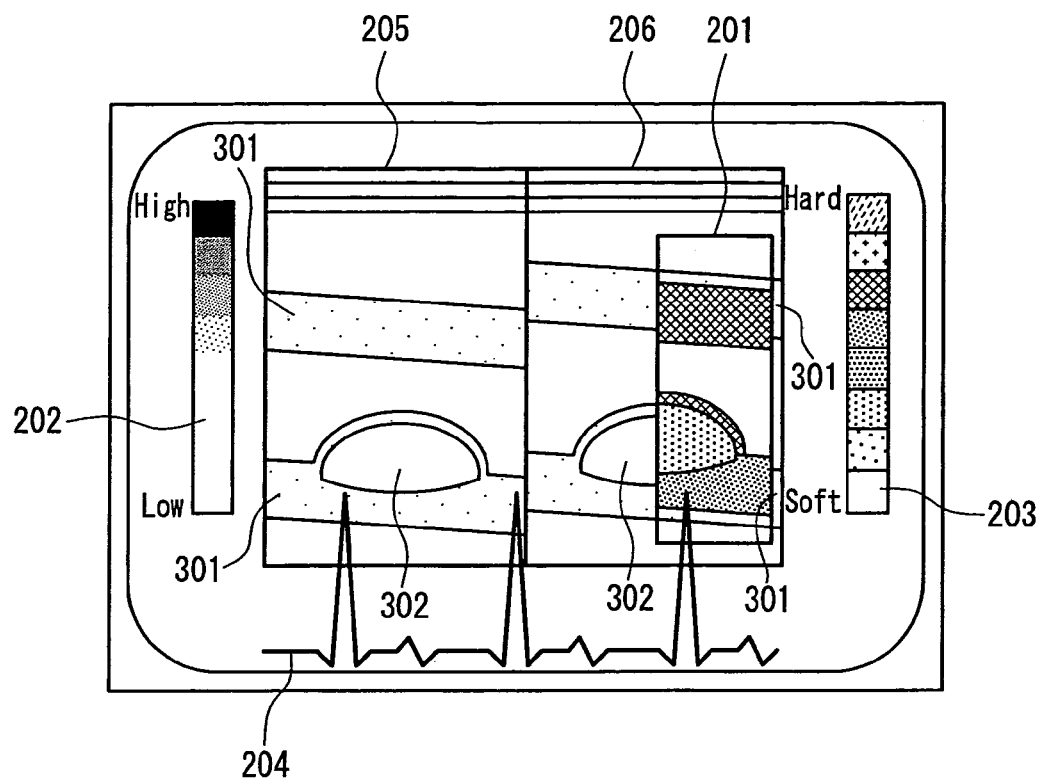
FIG. 7 is a diagram showing an example of a monitor display screen in a live mode in an ultrasonic diagnostic apparatus according to Embodiment 2 of the present invention.
Figure 8:
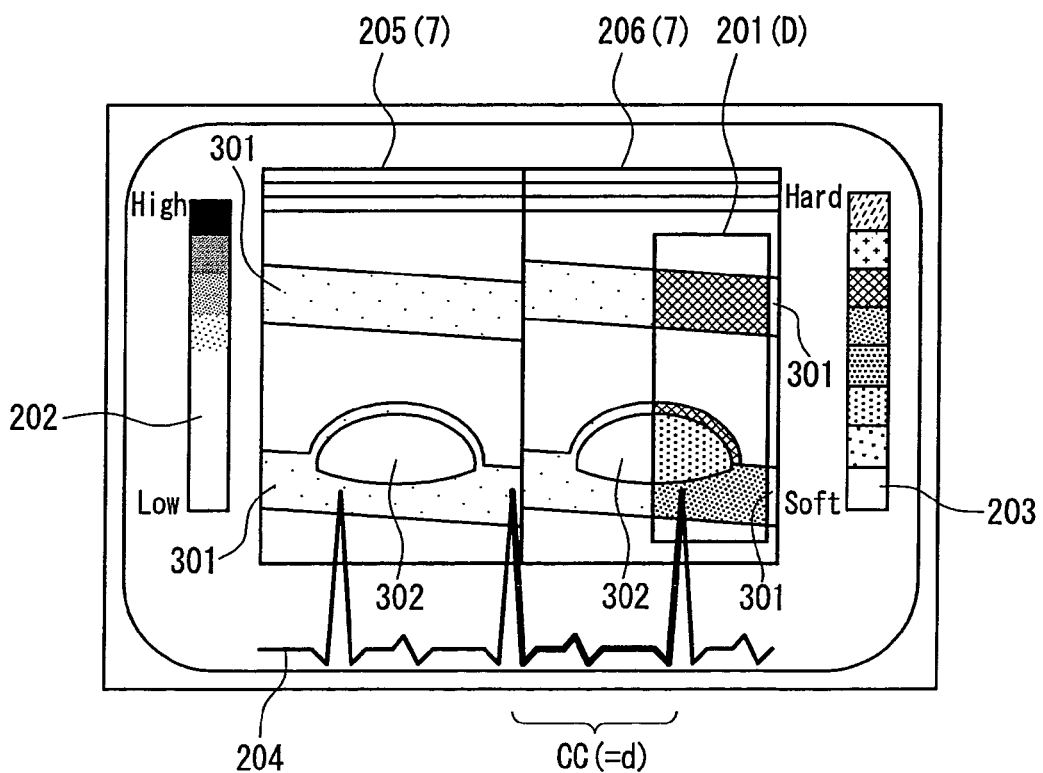
FIG. 8 is a diagram showing an example of a monitor display screen in a cine mode in the ultrasonic diagnostic apparatus according to Embodiment 2 of the present invention.
Figure 9:
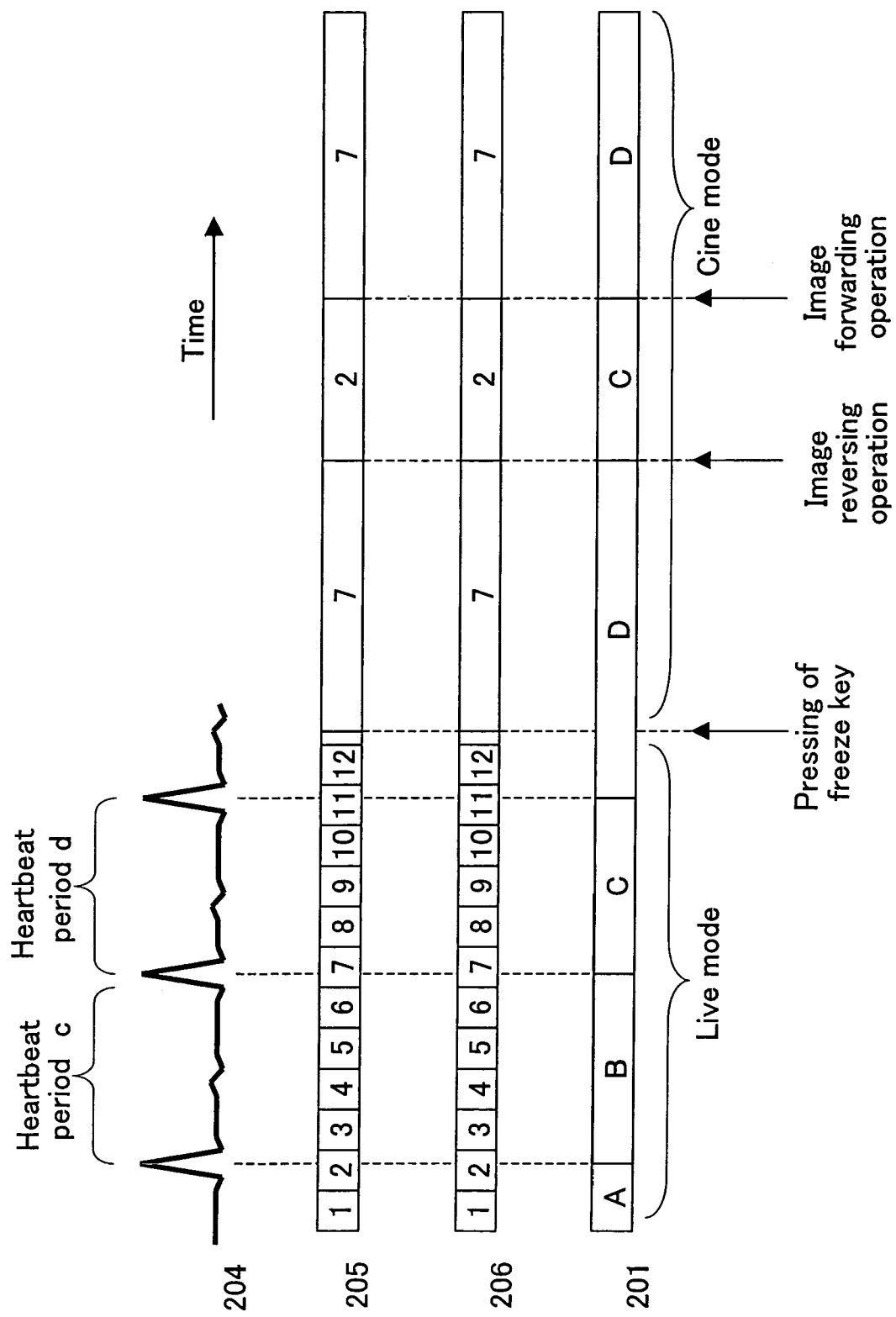
FIG. 9 is a timing chart showing an electrocardiographic or phonocardiographic waveform, left-side tomographic image display frames, right-side tomographic image display frames, and elastic-modulus-image display frames according to Embodiment 2 of the present invention.

FIG. 7 shows a display screen of the monitor 107 in a live mode, and FIG. 8 shows a display screen of the monitor 107 in the case where an image reversing operation is performed in a cine mode. FIG. 9 is a timing chart showing an electrocardiographic or phonocardiographic waveform 204, display frames of a left-side tomographic image 205 on which an elastic modulus image 201 is not superimposed, display frames of a right-side tomographic image 206 on which the elastic modulus image 201 is superimposed, and display frames of the elastic modulus image 201, which are displayed on the monitor 107 in the live mode and the cine mode.

In FIG. 9, as for the right-side tomographic image 206 on which the elastic modulus image 201 is superimposed, the same applies as in Embodiment 1. Meanwhile, in the cine mode, the display frames of the left-side tomographic image 205 are in synchronization with the display frames of the elastic modulus image 201.

As described above, a display screen is divided into two, and thus a portion hidden by the elastic modulus image 201 also can be viewed at the same time. Therefore, in the live mode, a probe operation such as for positioning and operations of setting various values such as a gain can be performed more easily. Further, in the cine mode, a tomographic image and a elastic modulus image that coincide with each other in time phase can be obtained at the same time, and thus by comparing the tomographic image with the elastic modulus image, the relationship between a structure and an elastic modulus of a subject tissue can be grasped easily.

Figure 10:
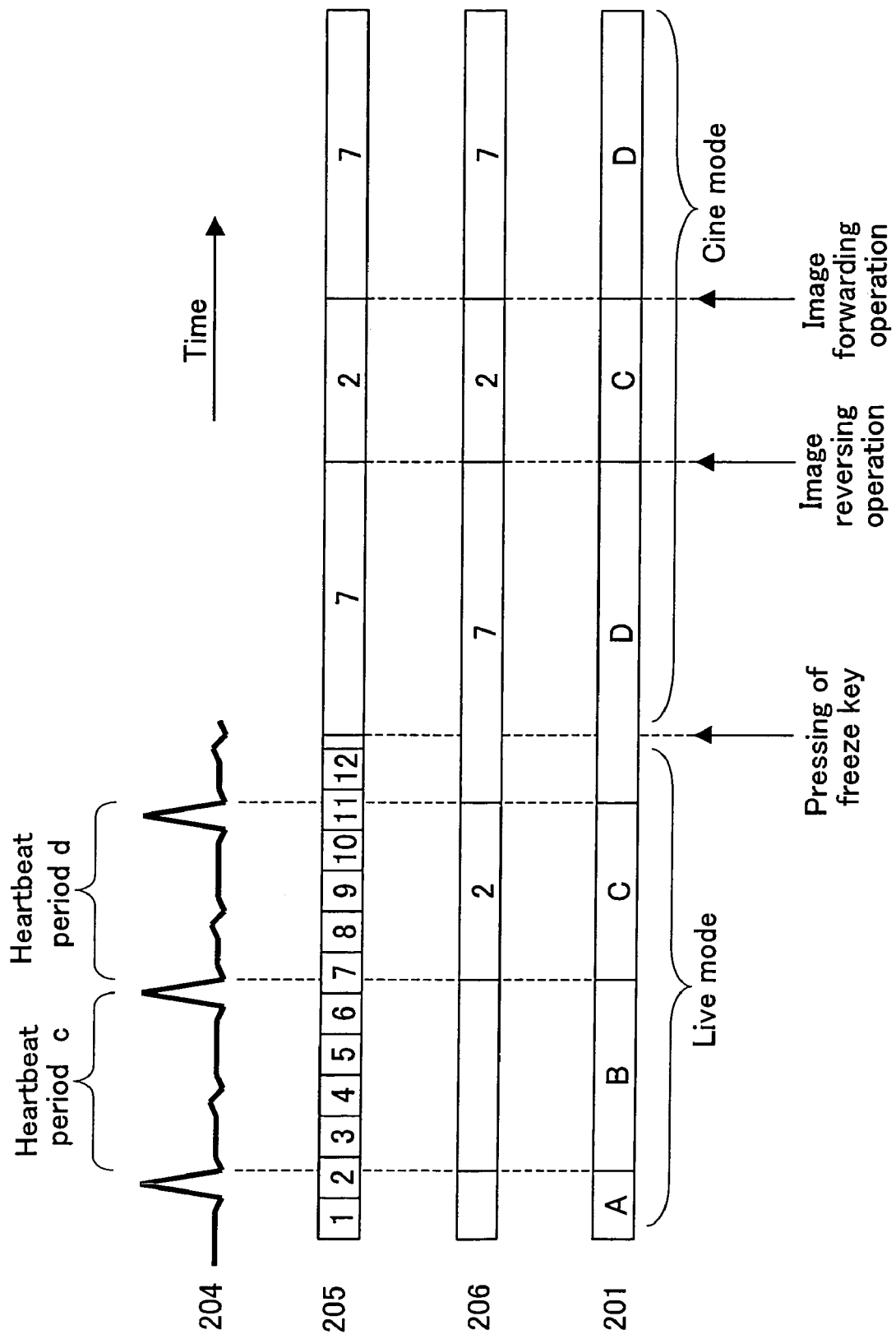
FIG. 10 is a timing chart showing an electrocardiographic or phonocardiographic waveform, left-side tomographic image display frames, right-side tomographic image display frames, and elastic-modulus-image display frames according to a modification of Embodiment 2 of the present invention.

FIG. 10 is a timing chart showing the electrocardiographic or phonocardiographic waveform 204, display frames of the left-side tomographic image 205 on which the elastic modulus image 201 is not superimposed, display frames of the right-side tomographic image 206 on which the elastic modulus image 201 is superimposed, and display frames of the elastic modulus image 201, which are displayed on the monitor 107 in the live mode and the cine mode, according to a modification of this embodiment.

Referring to FIG. 10, even in the live mode, a display frame 2 of the right-side tomographic image 206 is in synchronization with a display frame C of the elastic modulus image 201. An operation performed in the cine mode is the same as in the case shown in FIG. 9.

As described above, according to the modification of this embodiment, even in a live mode, a tomographic image and the elastic modulus image 201 that are in conformity with each other in terms of a positional relationship between a structure and an elastic modulus of a subject tissue are displayed in the right-side display region for the right-side tomographic image 206, thereby allowing a diagnosis result to be obtained immediately.

Figure 11:
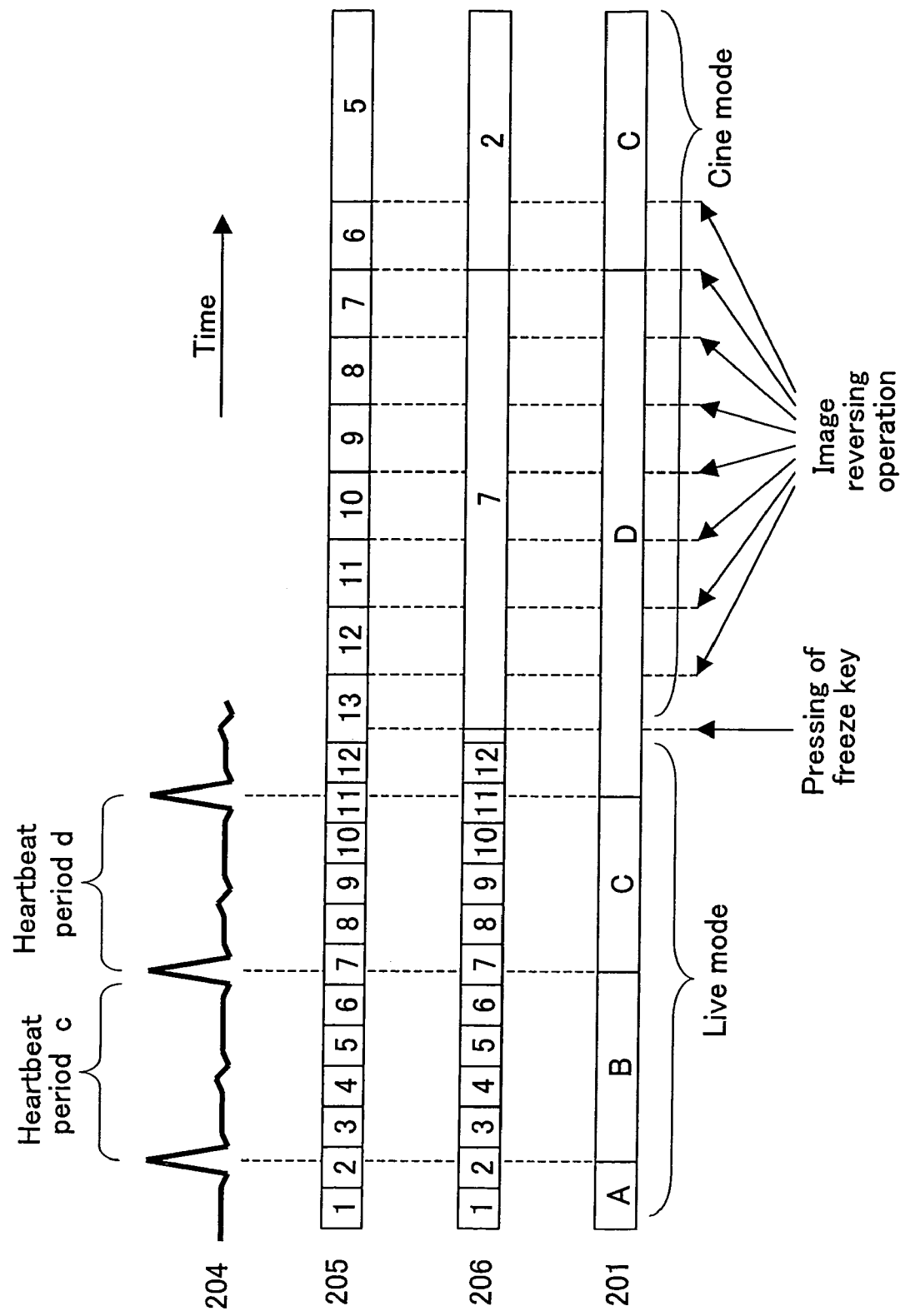
FIG. 11 is a timing chart showing an electrocardiographic or phonocardiographic waveform, left-side tomographic image display frames, right-side tomographic image display frames, and elastic-modulus-image display frames according to another modification of Embodiment 2 of the present invention.
Figure 12:
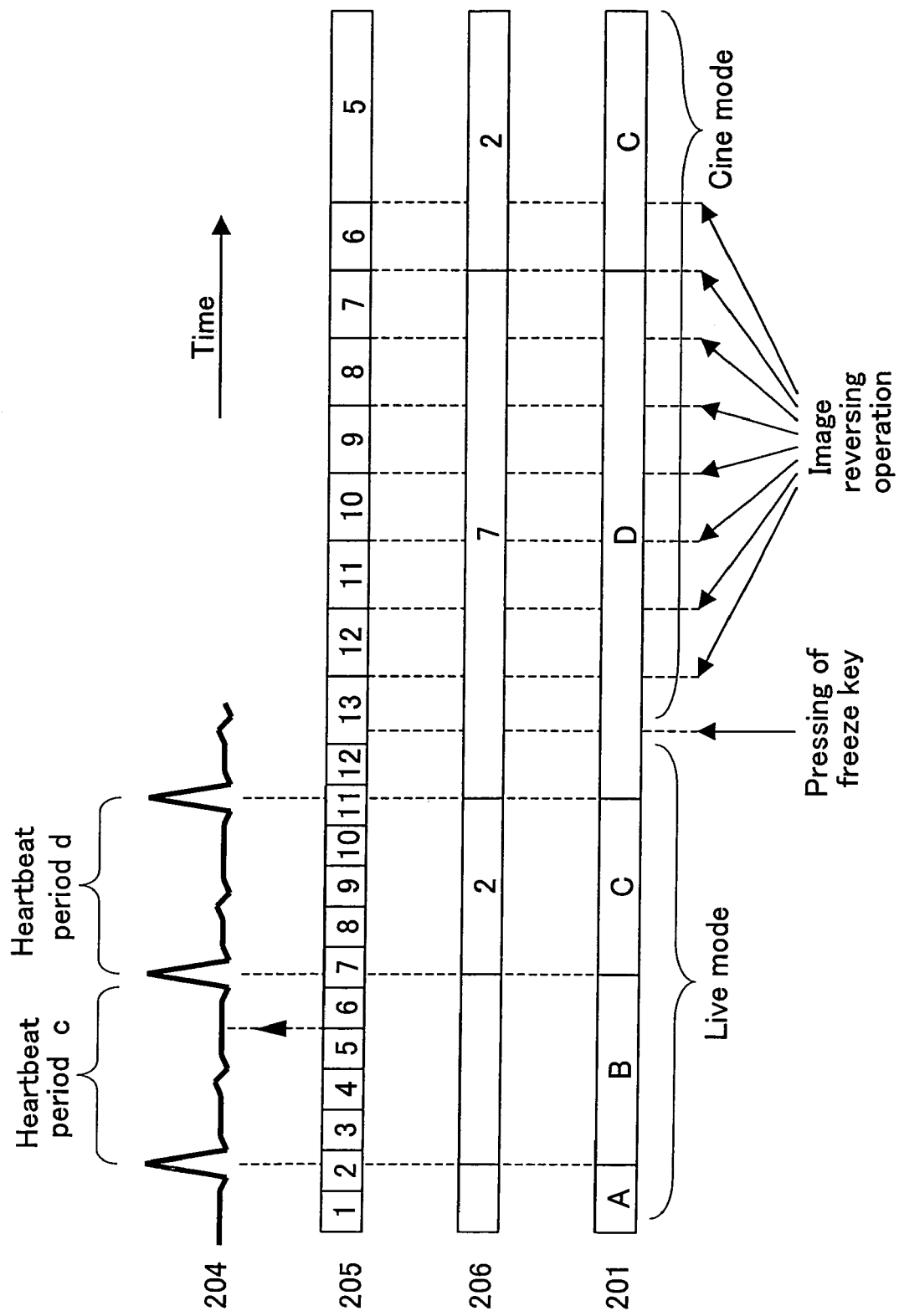
FIG. 12 is a timing chart showing an electrocardiographic or phonocardiographic waveform, left-side tomographic image display frames, right-side tomographic image display frames, and elastic-modulus-image display frames according to still another modification of Embodiment 2 of the present invention.

Each of FIGS. 11 and 12 is a timing chart showing the electrocardiographic or phonocardiographic waveform 204, display frames of the left-side tomographic image 205 on which the elastic modulus image 201 is not superimposed, display frames of the right-side tomographic image 206 on which the elastic modulus image 201 is superimposed, and display frames of the elastic modulus image 201, which are displayed on the monitor 107 in the live mode and the cine mode, according to each of other modifications of this embodiment. Operations in the live mode shown in FIGS. 11 and 12 are the same as those shown in FIGS. 9 and 10, respectively. The following mainly describes the differences.

Firstly, right after a shift to the cine mode is performed by pressing of a freeze key, referring to FIG. 11 or FIG. 12, in the right-side display region for the right-side tomographic image 206, a display frame D of a newest elastic modulus image and a display frame 7 of a tomographic image that corresponds thereto are displayed, while in the left-side display region for the left-side tomographic image 205, a display frame 13 of a newest tomographic image is displayed.

Next, when an image reversing operation is performed in the cine mode, in the left-side display region for the left-side tomographic image 205, an immediately preceding frame as a tomographic image is displayed sequentially by reading out from a tomographic image memory 110 (display frames 12, 11, 10, . . . ). Meanwhile, in the right-side display region for the right-side tomographic image 206, an elastic-modulus-image display frame 201(D) that is obtained based on a heartbeat period in which a frame being displayed as the left-side tomographic image 205 is included is displayed by reading out from an elastic-modulus-image memory 111, while a tomographic image display frame 206(7) that is in synchronization with the elastic-modulus-image display frame 201(D) is displayed by reading out from the tomographic image memory 110.

In this case, however, since a heartbeat period including the image at the timing when the freeze key is pressed is not completed, an elastic-modulus-image display frame obtained right before the heartbeat period and a tomographic image display frame corresponding thereto are displayed.

Thus, according to either of operations shown in FIGS. 11 and 12, every time an image reversing operation is performed, in the left-side display region for the left-side tomographic image 205, an immediately preceding frame as a tomographic image is displayed sequentially by reading out from the tomographic image memory 110. Meanwhile, in the right-side display region for the right-side tomographic image 206, only after a heartbeat period in which the left-side tomographic image 205 is included is shifted from d to c, that is, the left-side tomographic image 205 is changed from a display frame 7 to a display frame 6 and is displayed, the elastic-modulus-image display frame 201(D) and the tomographic image display frame 206(7) corresponding thereto are changed to an elastic-modulus-image display frame 201(C) and a tomographic image 206(2) corresponding thereto, respectively, and are displayed.

Figure 13:
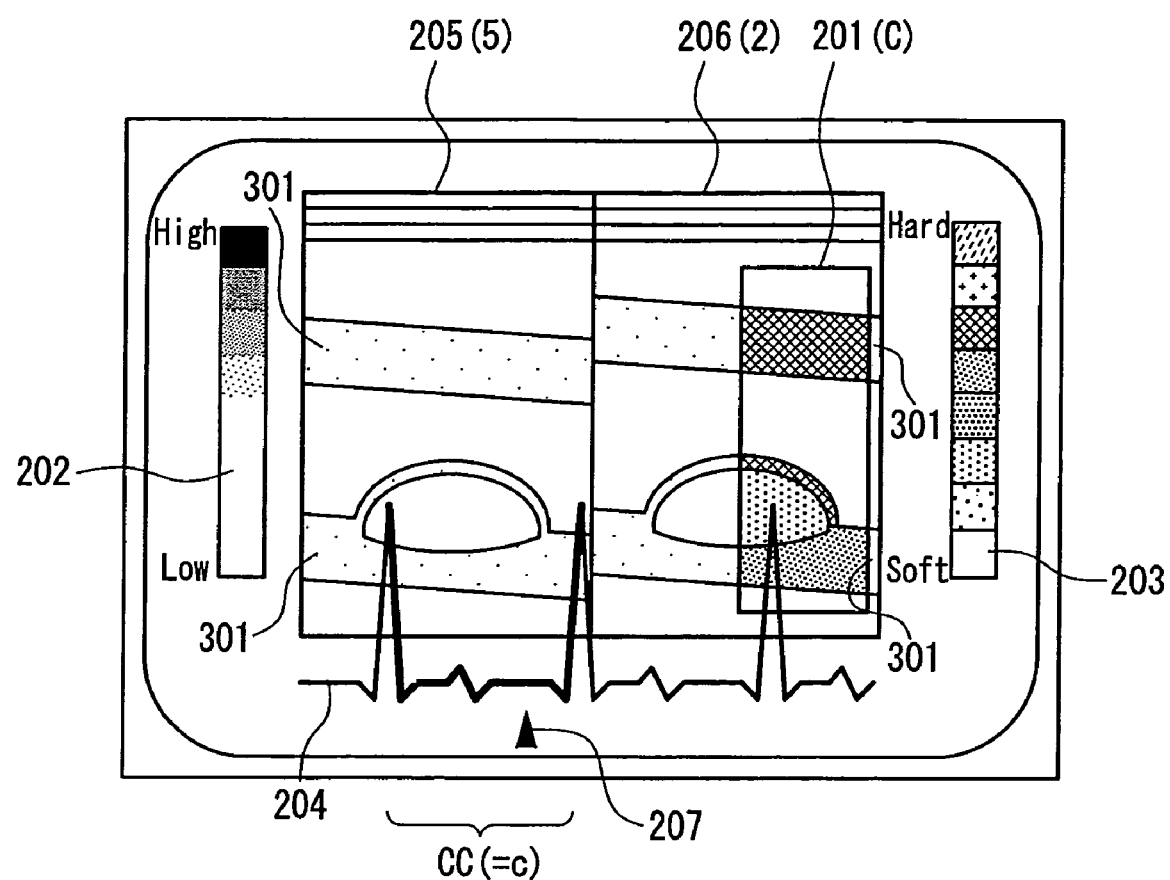
FIG. 13 is a diagram showing an example of a monitor display screen in a cine mode illustrated in FIG. 11 or FIG. 12.

FIG. 13 shows a display screen in the case where, as a result of performing an image reversing operation illustrated in FIG. 11 or FIG. 12, a change to the elastic-modulus-image display frame 201(C) and the tomographic image display frame 206(2) corresponding thereto is performed. In the left-side display region for the left-side tomographic image 205, a tomographic image display frame 205(5) is displayed, while in the right-side display region for the right-side tomographic image 206, the superimposed elastic-modulus-image display frame 201(C) and tomographic image display frame 206(2) are displayed. Further, a portion of the electrocardiographic waveform or phonocardiographic waveform 204 that corresponds to a heartbeat period in which an elastic modulus image being displayed is formed is displayed in a highlighted manner by means of a change in luminance or color tone (shown by a bold line in the figure), and a maker 207 that indicates a time phase of the display frame 205(5) of the left-side tomographic image 205 is displayed below the waveform.

As described above, according to the other modifications of this embodiment, in a left-side display region for the left-side tomographic image 205, a tomographic image can be displayed frame by frame, thereby allowing a detailed examination of a dynamic structural change of a subject tissue in a heartbeat period used for a calculation of an elastic modulus.

Similarly to Embodiment 1, by enabling ON/OFF switching between superimposed and non-superimposed states of the elastic modulus image 201 on the right-side tomographic image 206, a relationship between an elastic modulus and a structure can be grasped more easily.

Each of the embodiments of the present invention describes an ultrasonic diagnostic apparatus that calculates a strain of a subject tissue responsive to a change in blood pressure per heartbeat so as to determine an elastic modulus. However, the present invention also is applicable to an ultrasonic diagnostic apparatus that determines tissue characteristics of a subject such as a strain, a strain rate, an elastic modulus, a viscosity and the like of the tissue by calculation based on a change caused in a reception signal due to externally caused compression/relaxation or vibrations. In this case, preferably, a formation cycle of a tissue characteristic image is set so as to coincide with a cycle of the occurrence of the externally caused compression/relaxation or vibrations.

Furthermore, a one-dimensional waveform displayed on the display screen of the monitor 107 is not limited to an electrocardiographic or a phonocardiographic waveform. Various types of related waveforms can be displayed that include a waveform representing information on a subject such as a waveform of a blood pressure measured in real time and a waveform showing a change in internal diameter of a blood vessel, a tissue tracking waveform and a waveform showing a change in thickness of a tissue, and a waveform representing a progress in determining an elastic modulus such as a waveform showing a strain. Thus, in the case where a waveform representing information on a subject is displayed, it is possible to obtain the necessary information on the subject from one screen without referring to a separate display apparatus. Further, in the case where a waveform representing a progress is displayed, it is possible to perform a detailed observation of information used for conclusive determination of a tissue characteristic. That is, by allowing a waveform to be displayed that contains information corresponding to at least one of a tomographic image and a tissue characteristic image, effective referring to information related to an image being displayed is enabled. Moreover, a time period in which an elastic modulus image is formed can be displayed in a highlighted manner by various methods without any limitation to the use of a change in luminance or color tone. Such methods include the use of a different type of line such as a bold line, a thin line, a dotted line or the like and the enclosure with a square, parentheses or the like. Thus, information on a waveform corresponding to a time period in which an elastic modulus image is formed can be recognized at a glance.

INDUSTRIAL APPLICABILITY

According to the present invention, a tomographic image and a tissue characteristic image that are in conformity with each other in terms of time-phase and positional relationships can be displayed superimposedly, and thus an excellent ultrasonic diagnostic apparatus can be provided that enables an easy and detailed observation of a relationship between a structure and a characteristic of a subject tissue.

The invention claimed is:

1. An ultrasonic diagnostic apparatus, comprising:
ultrasonic wave transmission/reception means that transmits/receives an ultrasonic wave with respect to a subject;
a tomographic image processing part that forms a tomographic image representing a structure of the subject based on a reception signal;
a tissue characteristic image processing part that forms a tissue characteristic image representing a physical characteristic of a tissue of the subject through analysis of the reception signal of plural frames including at least one contraction and/or expansion period of the tissue;
memory means that stores the tomographic image and the tissue characteristic image, respectively;
an image composing part that combines at least the tomographic image and the tissue characteristic image;
display means that displays at least the tomographic image and the tissue characteristic image; and
control means for controlling an operation of the ultrasonic wave transmission/reception means, the tomographic image processing part, the tissue characteristic image processing part, the memory means, the image composing part and the display means,
wherein during an operation of the ultrasonic wave transmission/reception means, the control means is configured to allow the tomographic image to be renewed in an arbitrary cycle, displayed by the display means, and stored in the memory means, while allowing the tissue characteristic image to be renewed in a cycle different from the cycle for the tomographic image and corresponding to at least one contraction and/or expansion period of the tissue, allowing the tissue characteristic image obtained for a period at least one cycle before to be displayed by the display means, and allowing the tissue characteristic image to be stored in the memory means, and
during a suspension of the ultrasonic wave transmission/reception means, the control means is configured to allow an arbitrary one of the tissue characteristic images that have been acquired previously and one of the tomographic images that is in synchronization with the tissue characteristic image to be read out from the memory means, respectively and displayed by the display means.

2. The ultrasonic diagnostic apparatus according to claim 1, wherein the display means is divided into a first display region and a second display region, and displays at least the tomographic image in the first display region and at least the tomographic image on which the tissue characteristic image is superimposed in the second display region,
during the operation of the ultrasonic wave transmission/reception means, the control means is configured to allow the tomographic image to be displayed at least in the first display region of the display means, while allowing the tissue characteristic image to be displayed in the second display region of the display means, and
during the suspension of the ultrasonic wave transmission/reception means, the control means is configured to allow the tissue characteristic image and one of the tomographic images that is in synchronization with the tissue characteristic image to be read out from the memory means, respectively and displayed at least in the second display region of the display means.

3. The ultrasonic diagnostic apparatus according to claim 2, wherein during the operation of ultrasonic wave transmission/reception, one of the tomographic images that is in synchronization with the tissue characteristic image is displayed in the second display region.

4. The ultrasonic diagnostic apparatus according to claim 2, wherein during the suspension of ultrasonic wave transmission/reception, one of the tomographic images that is in synchronization with the tissue characteristic image is displayed in the first display region.

5. The ultrasonic diagnostic apparatus according to claim 2, wherein during the suspension of ultrasonic wave transmission/reception, the tissue characteristic image that is obtained based on a time period in which the tomographic image displayed in the first display region is included and the tomographic image that is in synchronization with the tissue characteristic image are displayed superimposedly in the second display region.

6. The ultrasonic diagnostic apparatus according to claim 1, wherein the image composing part allows a related waveform that contains information corresponding to at least one of the tomographic image and the tissue characteristic image to be displayed on a display screen of the display means in such a manner as to be combined with the tomographic image and the tissue characteristic image, and
during the suspension of ultrasonic wave transmission/reception, the control means allows a portion of the related waveform to be displayed in a highlighted manner, which corresponds to a time period in which the tissue characteristic image being displayed is formed.

7. The ultrasonic diagnostic apparatus according to claim 1, wherein the tissue characteristic image is an elastic modulus image.

8. The ultrasonic diagnostic apparatus according to claim 1, wherein the tissue characteristic image is an image representing a strain or a strain rate.

9. The ultrasonic diagnostic apparatus according to claim 1, wherein the tissue characteristic image is an image representing a viscosity.

* * * * *